(12) United States Patent
Le

(10) Patent No.: US 10,746,663 B2
(45) Date of Patent: Aug. 18, 2020

(54) METHODS AND APPARATUSES RELATING TO DERMAL BIOCHEMICAL SENSORS

(71) Applicant: DermaTec LLC, Albuquerque, NM (US)

(72) Inventor: Anh-Dung Le, Albuquerque, NM (US)

(73) Assignee: Dermatec LLC, Albuquerque, NM (US)

( * ) Notice: Subject to any disclaimer, the term of this patent is extended or adjusted under 35 U.S.C. 154(b) by 455 days.

(21) Appl. No.: 15/434,361

(22) Filed: Feb. 16, 2017

(65) Prior Publication Data

US 2017/0248524 A1    Aug. 31, 2017

Related U.S. Application Data

(60) Provisional application No. 62/300,143, filed on Feb. 26, 2016.

(51) Int. Cl.
| | | |
|---|---|---|
| *A61B 5/145* | (2006.01) | |
| *G01N 21/78* | (2006.01) | |
| *A61B 5/00* | (2006.01) | |
| *G01N 21/77* | (2006.01) | |

(52) U.S. Cl.
CPC ............. *G01N 21/78* (2013.01); *A61B 5/441* (2013.01); *A61B 5/4845* (2013.01); *A61B 5/6833* (2013.01); *A61B 5/14546* (2013.01); *G01N 2021/7796* (2013.01)

(58) Field of Classification Search
CPC ... G01N 2021/7756; G01N 2021/7796; G01N 21/78; A61B 5/441; A61B 5/4845; A61B 5/6833; A61B 5/14546

USPC ................. 600/362, 346, 366, 365
See application file for complete search history.

(56) References Cited

U.S. PATENT DOCUMENTS

| | | | | |
|---|---|---|---|---|
| 3,552,929 A | * | 1/1971 | Fields et al. | A61B 5/441 422/424 |
| 4,821,733 A | * | 4/1989 | Peck | A61B 5/14521 600/361 |
| 4,957,108 A | * | 9/1990 | Schoendorfer | A61B 5/418 600/362 |
| 5,076,273 A | * | 12/1991 | Schoendorfer | A61B 5/14521 600/573 |
| 5,139,023 A | * | 8/1992 | Stanley | A61B 5/14532 600/368 |
| 5,203,327 A | * | 4/1993 | Schoendorfer | A61B 5/14521 600/309 |
| 5,332,548 A | * | 7/1994 | Moore | G01N 31/223 422/421 |

(Continued)

*Primary Examiner* — Navin Natnithithadha
(74) *Attorney, Agent, or Firm* — V Gerald Grafe

(57) ABSTRACT

Example embodiments of the present invention comprise an analyte sensing patch, comprising a substrate, and a sensing agent disposed on the substrate such that analyte can encounter the sensing agent through a side of the patch disposed adjacent the skin of a subject but not through a side of the patch disposed away from the skin of the subject. Example embodiments of the present invention comprise an analyte sensing patch, comprising a substrate, a sensing material disposed on the substrate in a first region thereof, an adhesive disposed on the substrate in a second region thereof, wherein the second region surrounds the first region, wherein the sensing agent undergoes a change in a discernible characteristic responsive to encounter with a predetermined analyte.

10 Claims, 7 Drawing Sheets

(56) References Cited

U.S. PATENT DOCUMENTS

| | | | | |
|---|---|---|---|---|
| 5,438,984 A * | 8/1995 | Schoendorfer | A61B 5/14521 | 600/346 |
| 5,441,048 A * | 8/1995 | Schoendorfer | A61B 5/14521 | 600/346 |
| 5,443,080 A * | 8/1995 | D'Angelo | A61B 5/14514 | 600/362 |
| 5,462,064 A * | 10/1995 | D'Angelo | A61B 5/14514 | 424/449 |
| 5,465,713 A * | 11/1995 | Schoendorfer | A61B 5/411 | 600/346 |
| 5,638,815 A * | 6/1997 | Schoendorfer | A61B 5/14521 | 600/346 |
| 5,676,144 A * | 10/1997 | Schoendorfer | A61B 5/411 | 600/362 |
| 5,817,011 A * | 10/1998 | Schoendorfer | A61B 5/14521 | 600/362 |
| 5,817,012 A * | 10/1998 | Schoendorfer | A61B 10/0035 | 600/362 |
| 5,944,662 A * | 8/1999 | Schoendorfer | A61B 5/14521 | 600/362 |
| 6,042,543 A * | 3/2000 | Warwick | A61B 5/4266 | 422/424 |
| 6,479,015 B1 * | 11/2002 | Long | C12Q 1/26 | 422/419 |
| 6,503,198 B1 * | 1/2003 | Aronowtiz | A61B 5/14532 | 600/365 |
| 6,887,202 B2 * | 5/2005 | Currie | A61B 5/0059 | 600/309 |
| 7,700,305 B2 * | 4/2010 | Toranto | C12Q 1/26 | 422/412 |
| 7,931,592 B2 * | 4/2011 | Currie | A61B 5/0059 | 600/309 |
| 8,067,188 B2 * | 11/2011 | Toranto | C12Q 1/26 | 424/520 |
| 8,323,914 B2 * | 12/2012 | Toranto | C12Q 1/26 | 424/520 |
| 8,568,315 B2 * | 10/2013 | Currie | A61B 5/0059 | 600/309 |
| 9,332,937 B2 * | 5/2016 | Currie | A61B 5/0059 | |
| 9,719,124 B2 * | 8/2017 | Moriyama | C12Q 1/04 | |
| 10,023,898 B2 * | 7/2018 | Moriyama | C12Q 1/10 | |
| 2003/0175992 A1 * | 9/2003 | Toranto | G01N 33/487 | 436/514 |
| 2003/0175993 A1 * | 9/2003 | Toranto | G01N 33/487 | 436/518 |
| 2003/0225362 A1 * | 12/2003 | Currie | A61B 5/0059 | 604/20 |
| 2005/0182307 A1 * | 8/2005 | Currie | A61B 5/0059 | 600/300 |
| 2006/0004271 A1 * | 1/2006 | Peyser | A61B 5/14521 | 600/362 |
| 2007/0027383 A1 * | 2/2007 | Peyser | A61B 5/14521 | 600/347 |
| 2010/0063372 A1 * | 3/2010 | Potts | A61B 5/14521 | 600/346 |
| 2010/0075359 A1 * | 3/2010 | Toranto | C12Q 1/26 | 435/28 |
| 2010/0255497 A1 * | 10/2010 | Toranto | C12Q 1/26 | 435/7.1 |
| 2012/0010487 A1 * | 1/2012 | Currie | A61B 5/0059 | 600/365 |
| 2012/0034639 A1 * | 2/2012 | Toranto | C12Q 1/26 | 435/28 |
| 2012/0165626 A1 * | 6/2012 | Irina | A61B 5/14517 | 600/316 |
| 2014/0025000 A1 * | 1/2014 | Currie | A61B 5/0059 | 604/66 |
| 2017/0231571 A1 * | 8/2017 | Rogers | A61B 5/6833 | 600/301 |

* cited by examiner

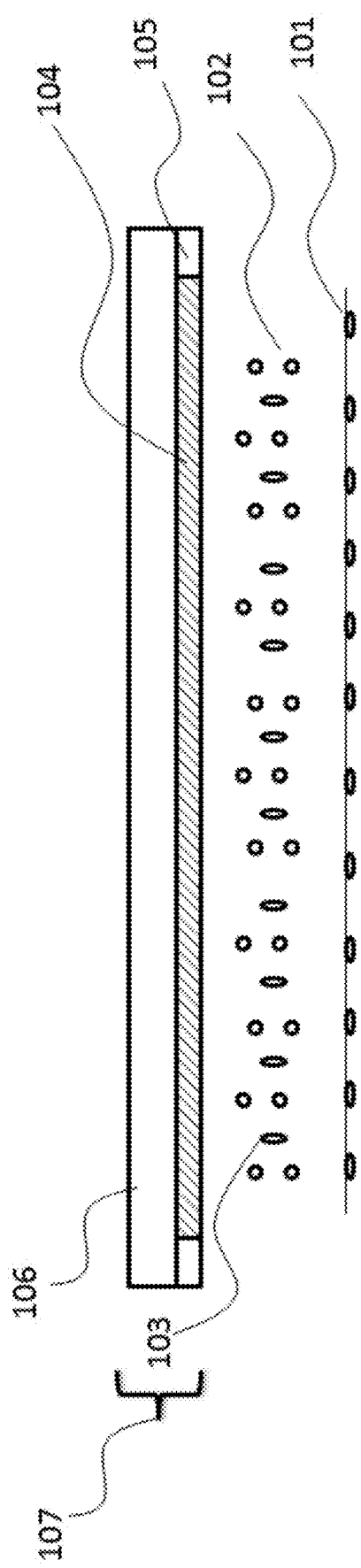
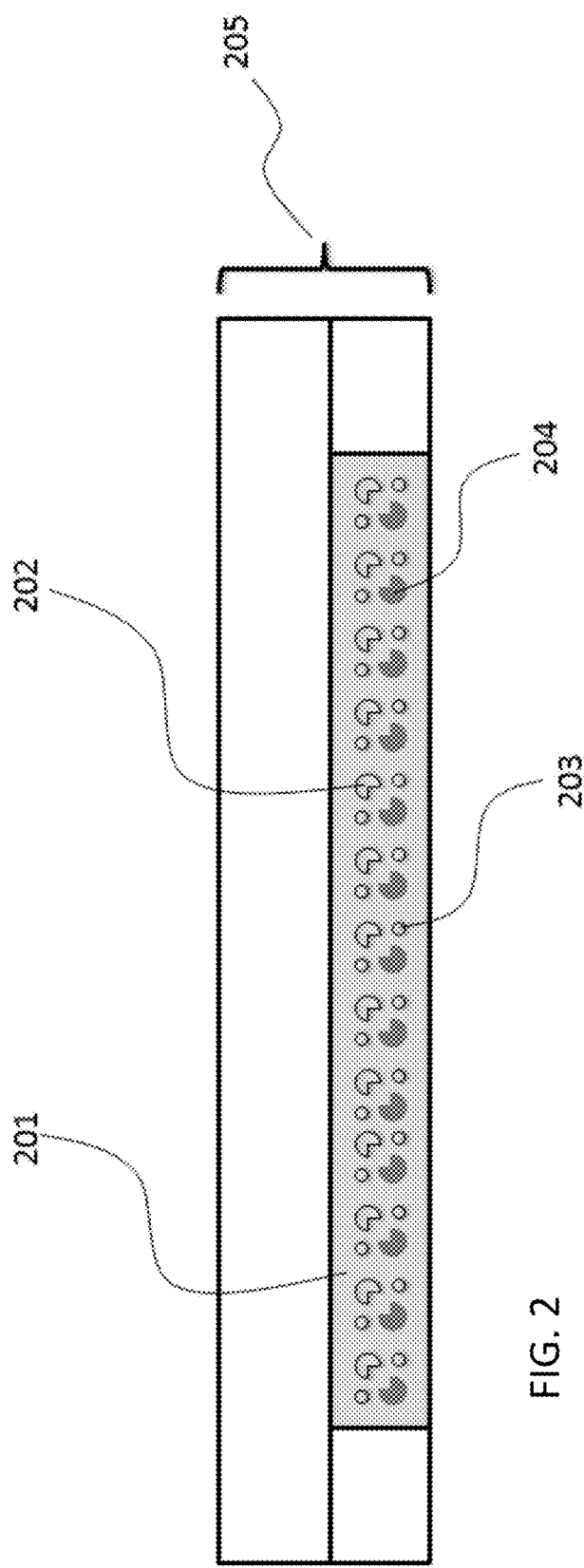
FIG. 1
FIG. 2

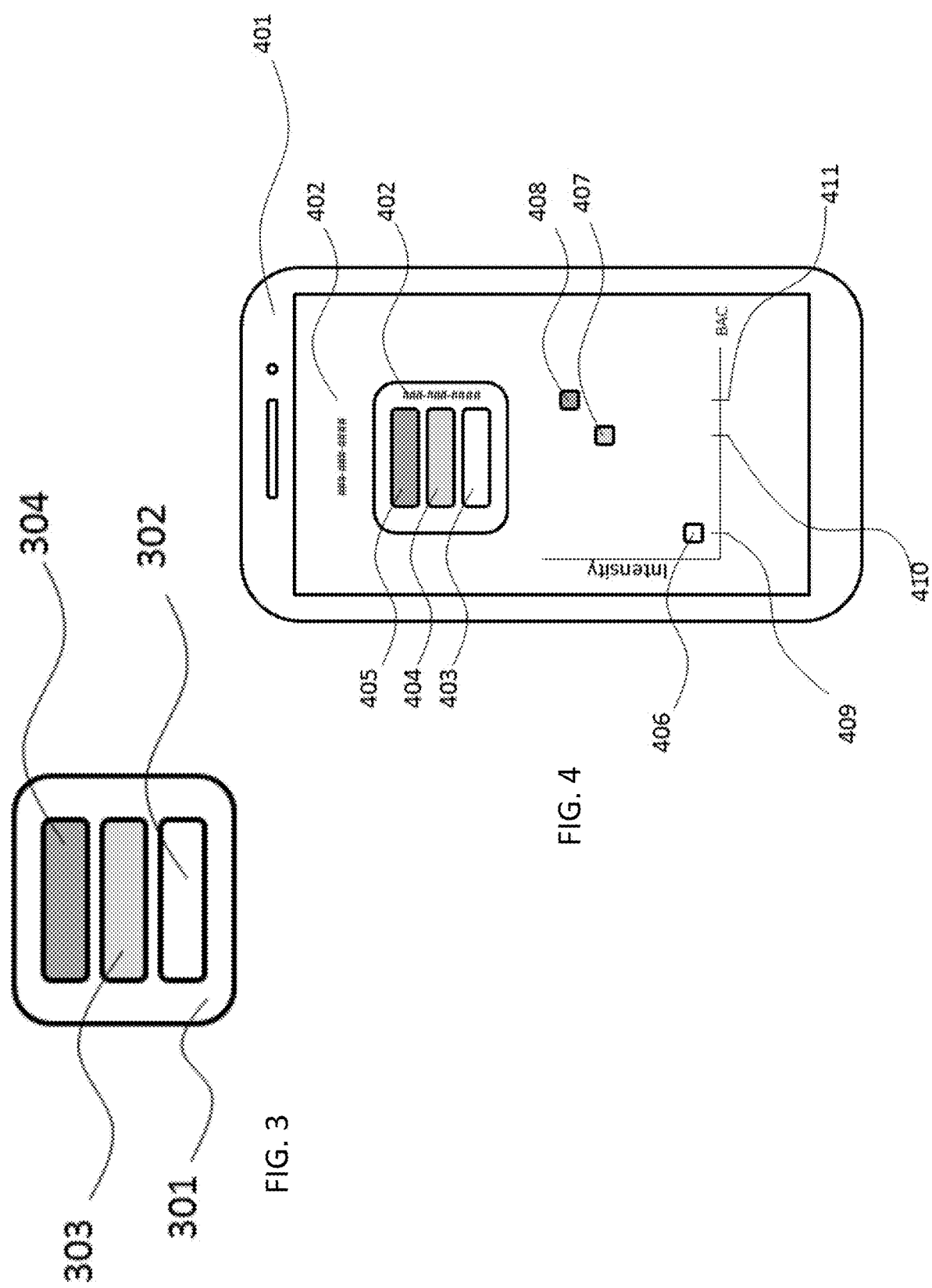

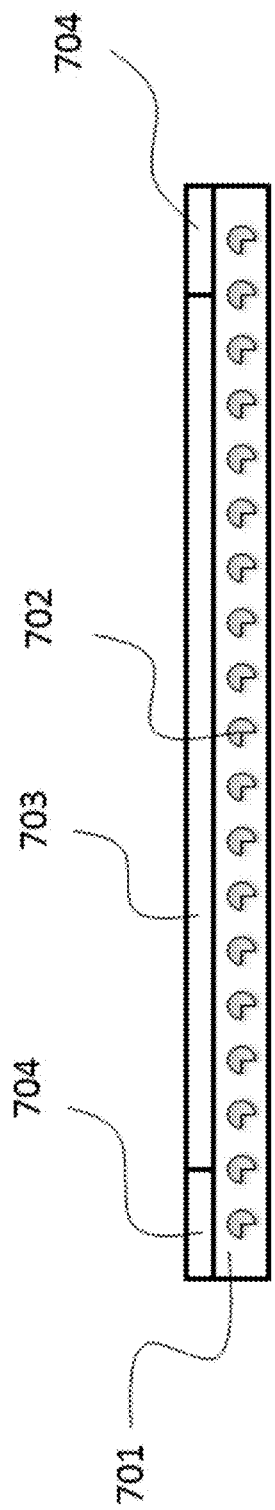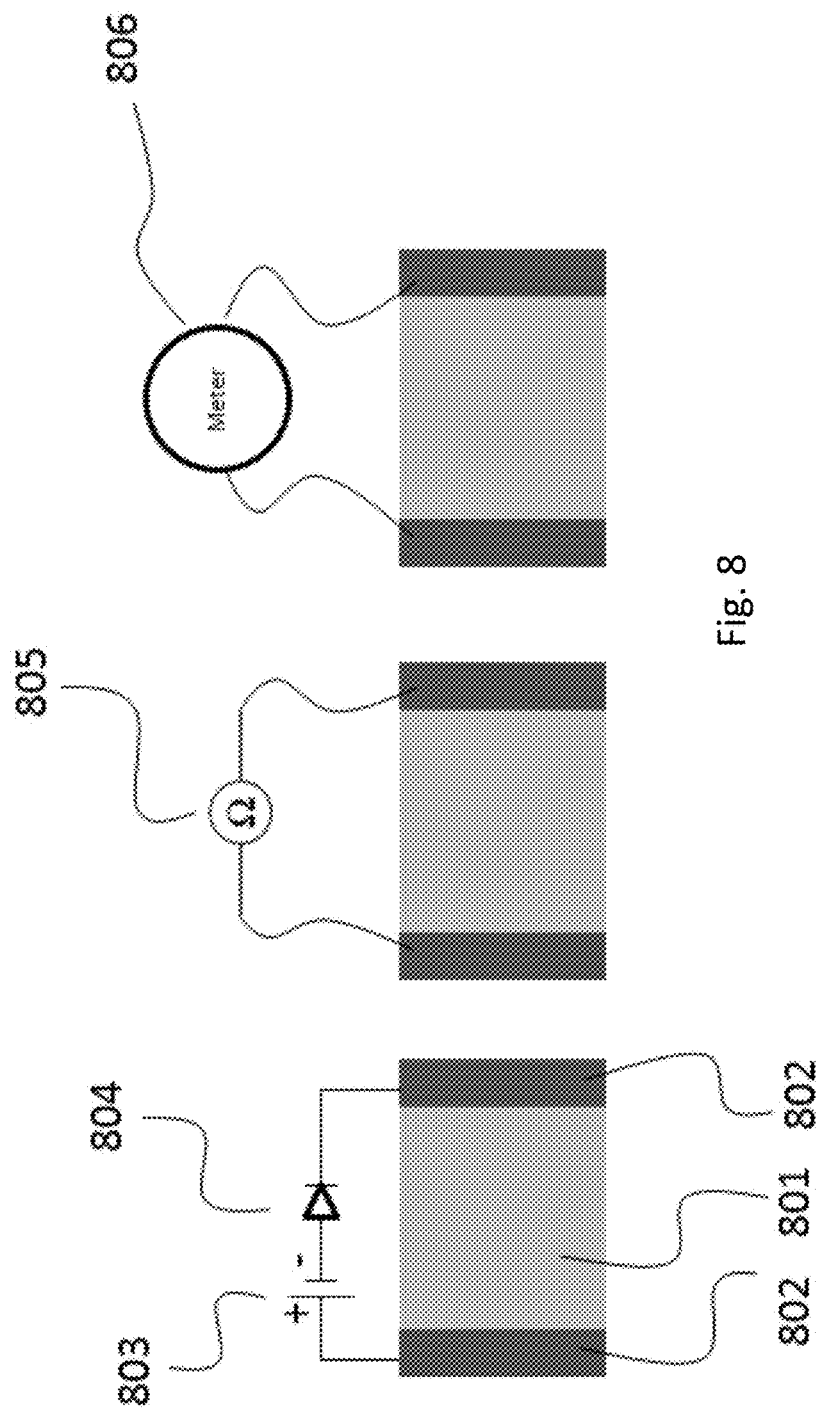

METHODS AND APPARATUSES RELATING TO DERMAL BIOCHEMICAL SENSORS

CROSS REFERENCE TO RELATED APPLICATIONS

The present application claims priority to U.S. provisional application 62/300,143, filed Feb. 26, 2016, which is incorporated herein by reference.

TECHNICAL FIELD

The present application relates to the field of transdermal sensing, and example embodiments relate more specifically to transdermal sensing of alcohol using patches applied to the skin.

SUMMARY OF THE INVENTION

Example embodiments of the present invention comprise an analyte sensing patch, comprising a substrate, and a sensing agent disposed on the substrate such that analyte can encounter the sensing agent through a side of the patch disposed adjacent the skin of a subject but not through a side of the patch disposed away from the skin of the subject. Example embodiments of the present invention comprise an analyte sensing patch, comprising a substrate, a sensing material disposed on the substrate in a first region thereof, an adhesive disposed on the substrate in a second region thereof, wherein the second region surrounds the first region, wherein the sensing agent undergoes a change in a discernible characteristic responsive to encounter with a predetermined analyte.

Embodiments of the present invention can be useful in detecting alcohol, for example in bar patrons or drivers, by simple examination of an unobtrusive patch. The simple patch allows real time, and repeated, monitoring of alcohol presence, eliminating the need for specially trained operators, expensive and obtrusive breath sample collectors or blood sample collectors, and bulky, expensive, or hazardous disposables such as breath tubes and needles.

DESCRIPTION OF THE DRAWINGS

An understanding of the features of the invention described below may be facilitated by reference to the appended drawings, which illustrate example methods and systems according to the invention, although it will be understood that such drawings depict example embodiments of the invention and, therefore, are not to be considered as limiting its scope with regard to other embodiments which the invention is capable of contemplating.

FIG. 1 is a schematic illustration of an example embodiment.

FIG. 2 is a schematic illustration of an example embodiment.

FIG. 3 is a schematic illustration of an example embodiment.

FIG. 4 is a schematic illustration of an example embodiment.

FIG. 7 is a schematic illustration of an example embodiment.

FIG. 8 is a schematic illustration of an example embodiment.

DESCRIPTION OF THE INVENTION

Figure 5:
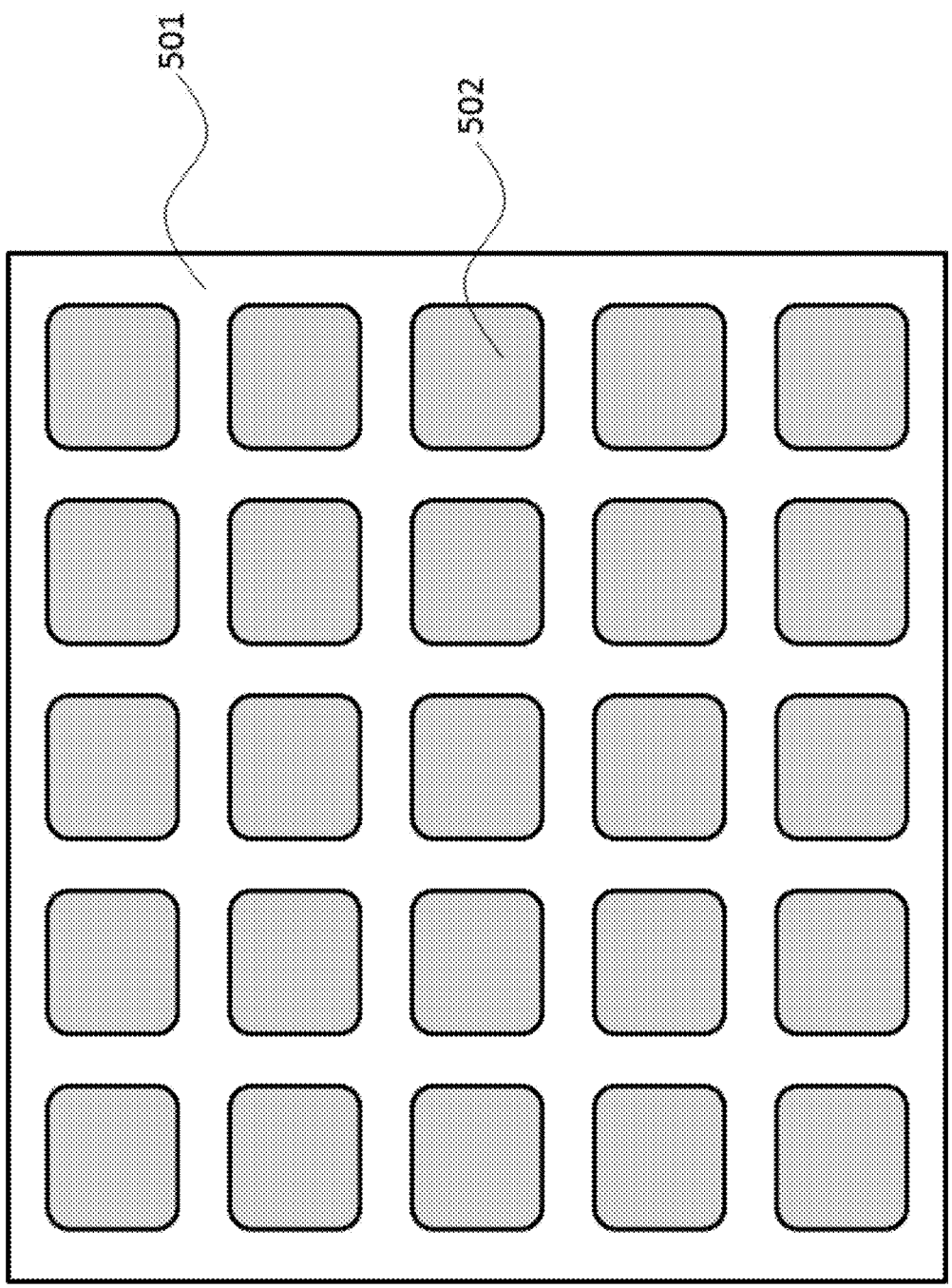
FIG. 5 is a schematic illustration of an example embodiment.

FIG. 1 is a schematic illustration of an example embodiment comprising a dermal patch. The overall patch 107 comprises a combined 2-layer system. Transmission channels 101 (e.g., sweat pores) in skin of a subject provide avenues through which biological or chemical analytes (generally referred to herein as analytes) can escape. Analytes can escape across the sweat pores together with physical perspiration (103) or through diffusion where no sweat can be noticed as seen in 102. Ethanol is an example analyte. Ethanol can be detected in sweat and also can be detected through diffusion due to its volatility. A patch cover 106 can comprise polyurethane or other material suitable for the intended application. Examples of suitable materials for applications such as ethanol sensing include Tegaderm dressings by 3M, and various Mediderm grades by Mylan, and any polymeric material typically used in transdermal patches (the foregoing are trademarks of their respective owners). Transdermal patch materials, as examples, can be suitable since they can adhere well to the skin while maintaining comfort and user friendliness. An adhesive layer comprises first 104 and second portions 105. First portion 104 comprises a portion of the adhesive that contains an active detecting material (ADM) while second portion 105 does not have the ADM. Surrounding the ADM portion 104 with a non-sensing portion 105 can prevent the ADM from encountering analytes or contaminants from the environment, and compromising the integrity of the sensing of analytes from the skin. Non-sensing portion 105 can be considered as a blank adhesive; where blank indicates no active detecting material.

FIG. 2 is a schematic illustration of an example embodiment 205 of a dermal patch containing an ADM system. An example of the ADM system contains an alcohol oxidase 204, peroxidase 202, and a chromogenic substrate 203. The ADM system is embedded in an adhesive 201. A primary alcohol oxidase will catalyze a reaction containing a primary alcohol such as ethanol and oxygen to produce an aldehyde and hydrogen peroxide. Peroxidase will catalyze a reaction containing hydrogen peroxide and a chromogenic substrate to produce water and the oxidized version of the chromogenic substrate. An example of a chromogenic substrate is 3,3',5,5'-Tetramethylbenzidine (TMB). However, other substrates can be used, for example, to yield different colors.

FIG. 3 is a schematic illustration of an example embodiment seen from the side of a patch opposite the skin. The patch comprises a polymeric material 301. A sensing region 303 contains an ADM as described elsewhere herein. A lower limit control region 302 is configured (e.g., colored) to correspond to the lower limit of detection of the ADM. An upper limit control region 304 is configured (e.g., colored) to correspond to the upper limit of detection of the ADM. For example, if the ADM changes color when exposed to the analyte of interest, then lower limit control region can be colored to correspond to the color perceived when the ADM has encountered the minimal amount of analyte that can be detected; and the upper limit control region can be colored to correspond to the color perceived when the ADM has encountered the maximum amount of analyte that can be detected (e.g., the amount that saturates the ADM). The intensity of the color change resulting in detection of some amount of analyte in the ADM region 303 will fall somewhere between 302 and 304. This color intensity can be estimated based on the upper limit control region (304) and the lower limit control region (302). As an alternative, a single control region can be used, or more than two control regions can be used. The control region(s) can correspond to other portions of the sensing range of the ADM; for example a control region can be configured to correspond to the state of the ADM when a predetermined amount of analyte has been encountered by the ADM (e.g., corresponding to a blood alcohol content above a presumptive legal limit for driving).

FIG. 4 is a schematic illustration of an image of an example embodiment as captured on a device 401 such as a smart phone. The device can comprise any device that can capture an image or sense the state of the ADM. In some applications, the patch can comprise an identifier 402 such as a serial number to allow matching of the patch with an identified user, or a calibration legend to allow the device to interpret the state of the ADM. Such identifiers can comprise any combination of numbers, digits, symbols, or images as long as the device can interpret the identifier. The identifier can also be stored with an electronic profile of a corresponding user. The example embodiment comprises a lower limit control region 403 and an upper limit control region 405. The example embodiment also comprises an ADM region 404 which contains the ADM which can change color according to the amount of analyte detected. The intensity of the color change resulting in detection of some amount of analyte in 404 will fall somewhere between 403 and 405. This color intensity can be estimated based on the upper limit (405) and the lower limit (403). For example, if ethanol is the analyte of interest, in order to estimate the amount of analyte, the amount of blood alcohol concentration (BAC) must be defined for the upper limit (405) and the lower limit (403). The lower limit can be defined as 0% BAC which can be graphically shown at 406 correlating to 409 on the x-axis. The upper limit can be at any % BAC, for example selected by the entity that designs and/or markets the patch. The upper limit can be graphically shown at 408 correlating to 411 on the x-axis. The % BAC of the user can be estimated based on 404's intensity shown graphically at 407, which correlates to 410 on the x-axis. To numerically determine the intensity of the color, an image analysis tool can be used. Such tool can be purchased, obtained for free, or custom designed. One example of such a tool is ImageJ which can quantify the intensity of a color.

FIG. 5 is a schematic illustration of a plurality of patches viewed from the side that will be adjacent the skin of a subject. The patches comprise a bottom layer 502 that is the polymeric layer with adhesive. A masking layer 501 can be used to prevent the active chemicals from touching non-active areas. As an example, masking layer 501 can comprise a non-stick paper generally used as a backing for stickers. The number of openings in the mask can vary depending manufacturing capabilities. Also, the shape of the openings in the mask can be of any shape. These shapes can be, but are not limited to: squares, circles, ovals, triangles, hexagons, octagons, concentric circles, etc. After configuration of the ADM, the patches can be separated, for example but cutting or by making perforations to allow later separation by users.

Figure 6:
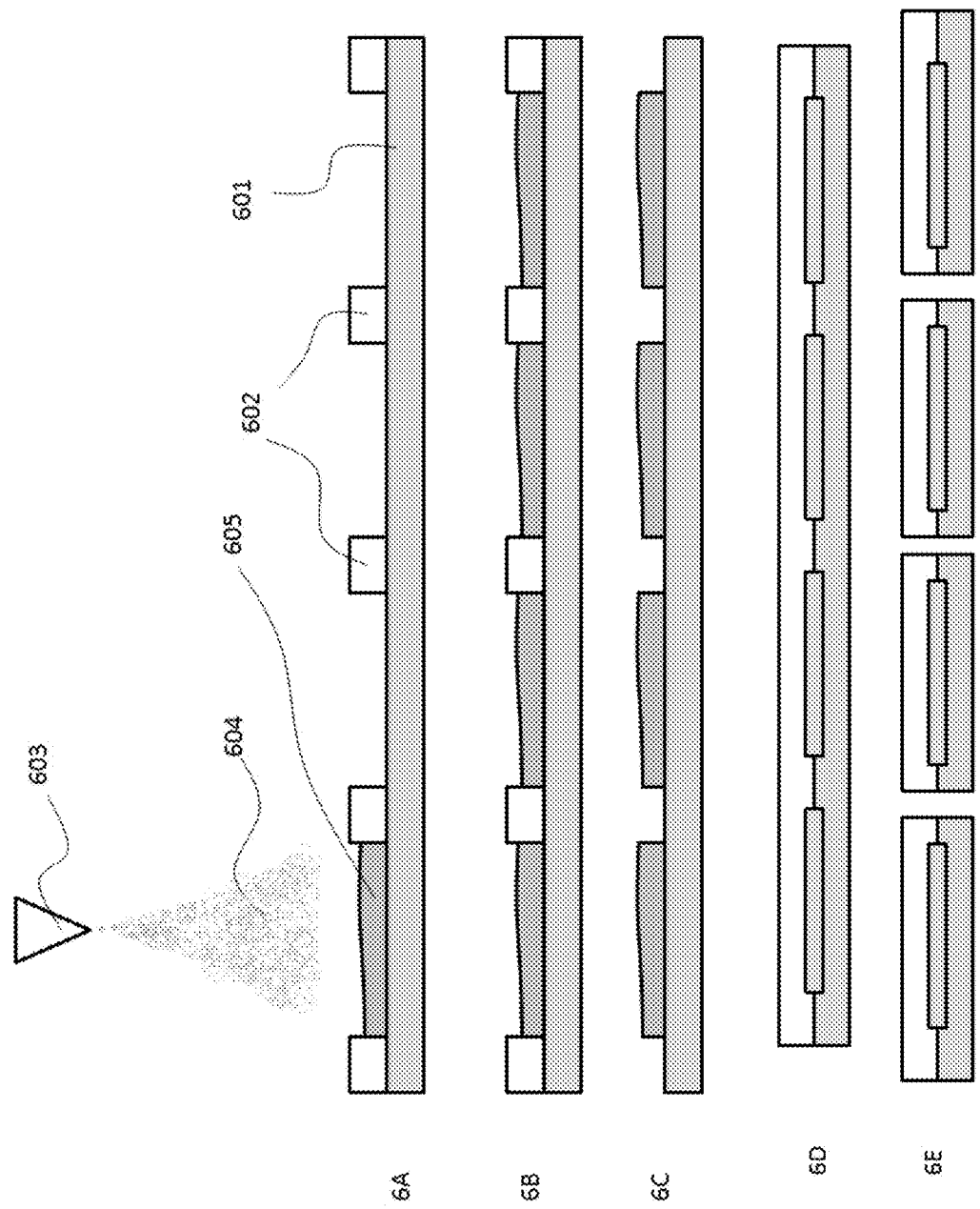
FIG. 6 is a schematic illustration of an example method according to the present invention.

FIG. 6 is a schematic illustration of an example method of making an array of chemically active patches according to the invention. In step 6A, a combined polymeric material 601 already has adhesive on top. The profile view shows a mask 602 on top blocking the sprayed chemical system at 604 coming from sprayer 603 from contacting the masked areas 602 of the polymeric material 601. Sprayer 603 can comprise any of various technologies suitable for applying chemicals to a substrate. Commercial airbrush systems or any other equipment suitable for the application of the chemicals on top of substrate 601 can be used. Furthermore, a paint brush can also be used to apply the active chemical system on top of substrate 601. Another example of equipment suitable for applying the active chemical system on top of substrate 601 can be a roller brush or similar versions suitable for use in manufacturing purposes. The layer 605 that rests on top of substrate 601 will be configured as the active sensing area.

Step 6B shows the resulting array with the coating process moving towards the uncoated areas. The mask at 602 blocked the applied material 604 from contacting the substrate surface at 601 in areas corresponding to the mask 602.

Step 6C shows the system after removal of the non-stick masking layer (602), for example by peeling it off. When mask 602 is removed, the resulting figure shows that the active areas 605 are deliberately separated.

Step 6D illustrates the placement of a second non-stick layer (possibly made of the same material as 602) on top of the resulting layer from 6C. The active areas are encapsulated and separated from each other by the substrate 601 and the section nonstick layer.

Step 6E illustrates the separation of the active areas. The different active areas can be separated by physical cutting in between their gaps resulting in the individual patches ready to be peeled off and used. Another way to prepare these patches to be ready for the consumer can be perforating in between these gaps and offered to the user in the form of rolls with individual patches tear-able from each other. In use, a user removes the second nonstick layer prior to applying the patch to the skin. The adhesive exposed by removal of the second nonstick layer adheres the patch to the skin, and maintains the active sensing region(s) in appropriate relation to the skin to receive analyte therefrom.

FIG. 7 is a schematic illustration of an example embodiment of a biosensor made from polyaniline (PANI) films (701) with an embedded enzyme at 702. If the analyte to be detected is ethanol, an example of the embedded enzyme can be alcohol oxidase. As mentioned above, alcohol oxidase will catalyze ethanol and oxygen into aldehyde and hydrogen peroxide. The presence of hydrogen peroxide will reduce the PANI film from its emeraldine salt form into emeraldine base, thus affecting the conductivity of the film. This means that measurement, directly or indirectly, of the conductivity of the film will provide information how much ethanol has been encountered by the sensing region. An insulator 703 will separate two conductive plates 704, e.g., metal, shown at two ends. A probe can be placed in communication with ends 704 to either directly or indirectly measure the conductivity of the PANI film.

FIG. 8 provides schematic illustrations of 3 example embodiments in the bird's eye view as different examples of ways to either measure directly or indirectly the conductivity of the PANI films. An insulating layer 801 is disposed on top of the PANI film. Conductive ends or metal plates 802 lie on top of the ends of the PANI film. A battery source 803 allows for a light emitting diode (LED) at 804 to light up depending on the characteristic or conductivity of the film. Another way to measure the conductivity of the film is connect the probes to any viable ohmmeter to determine the resistance between the conductive ends, as illustrated in the middle example in the figure. The measure of the resistance can inversely give information on the conductivity of the film. In another example embodiment, on the right in the figure, the probes are connected to a general meter 806. This meter can measure any characteristics of the film that can be indicative of the conductivity of the film. The meter can be any size and can be attached to a smart device. The meter can give a reading that can be translated to the current characteristic of the PANI film and provide information about the amount of analyte being measured.

Figure 9:
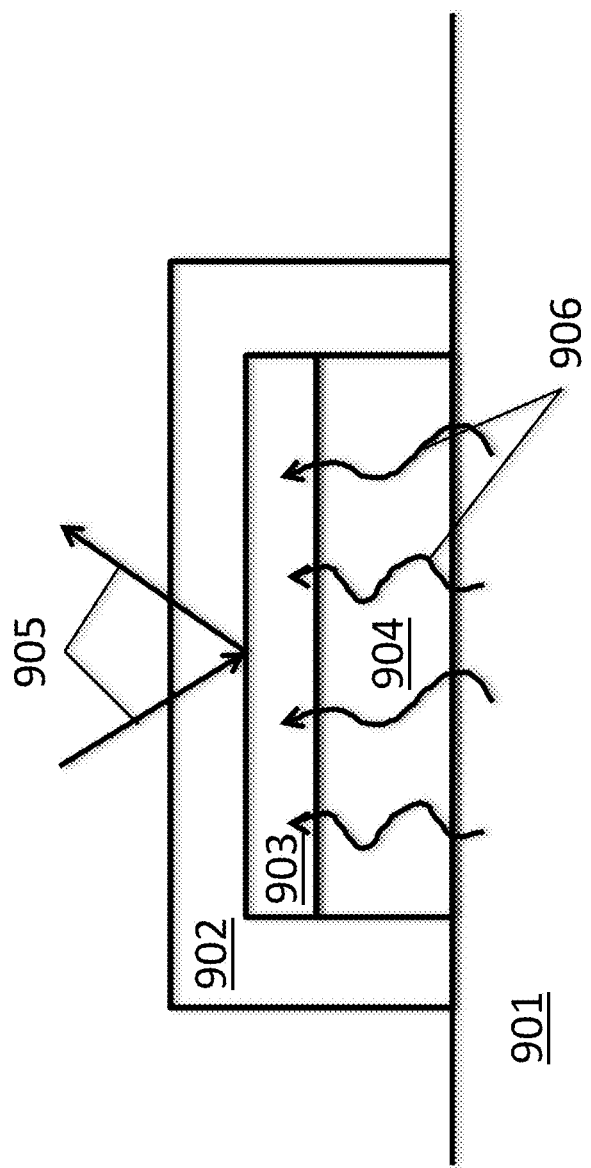
FIG. 9 is a schematic illustration of an example embodiment.

FIG. 9 is a schematic illustration of an example embodiment of the present invention. The embodiment is mounted with tissue 901, for example the skin, of a subject. A sensing region 903 of the embodiment comprises a material that experiences a change in an externally detectable characteristic responsive to encounters with an analyte of interest 906, e.g., ethanol, or a substance of abuse such an illegal drug, or a metabolically significant substance such as cholesterol or lactic acid. The sensing region 903 can be in direct physical contact with the tissue, or can be separated from the tissue by a layer 904 that provides protection for the sensing region or adhesion to the skin or more desirable analyte transport performance, or a combination thereof, while still allowing the analyte to affect the sensing region. A protective layer 902 surrounds the sensing region 903, preventing analytes or contaminants from outside the tissue from affecting the sensing region 903. An external reader (not shown) interrogates 905 the sensing region and determines the change in the characteristic of the sensing region responsive to encounter with the analyte.

The characteristic can comprise any characteristic that can be detected. Some examples are listed below. In most of the examples, a human can directly perform the sensing, although providing electrical, mechanical, or computer assistance can help in accurate analyte determinations. The sensing region can change reflectivity, and a light with a light capture device, such as a LED light and a camera on a smart phone or smart watch, can assess the change in reflectivity. The sensing region can change viscosity or stiffness or other mechanical property, and a physical sensor such as a touch sensor can assess the change in the mechanical property. The sensing region can change in physical volume, for example by expanding or contracting responsive to the analyte, and a sensing device can assess the change in size of the sensing region. Changes in volume or physical stiffness of the sensing region can cause a change in the appearance of a visible feature of the patch, e.g., by leaking sensing agent into a previously clear region as the sensing agent expands, or bending or straightening an indicator as the sensing agent becomes more or less stiff. Changes in color responsive to the analyte, such as described above, can also be used. A smart phone or similar device can be used to accurately assess even minor changes in physical property such as color, allowing very accurate analyte determinations.

Figure 10:
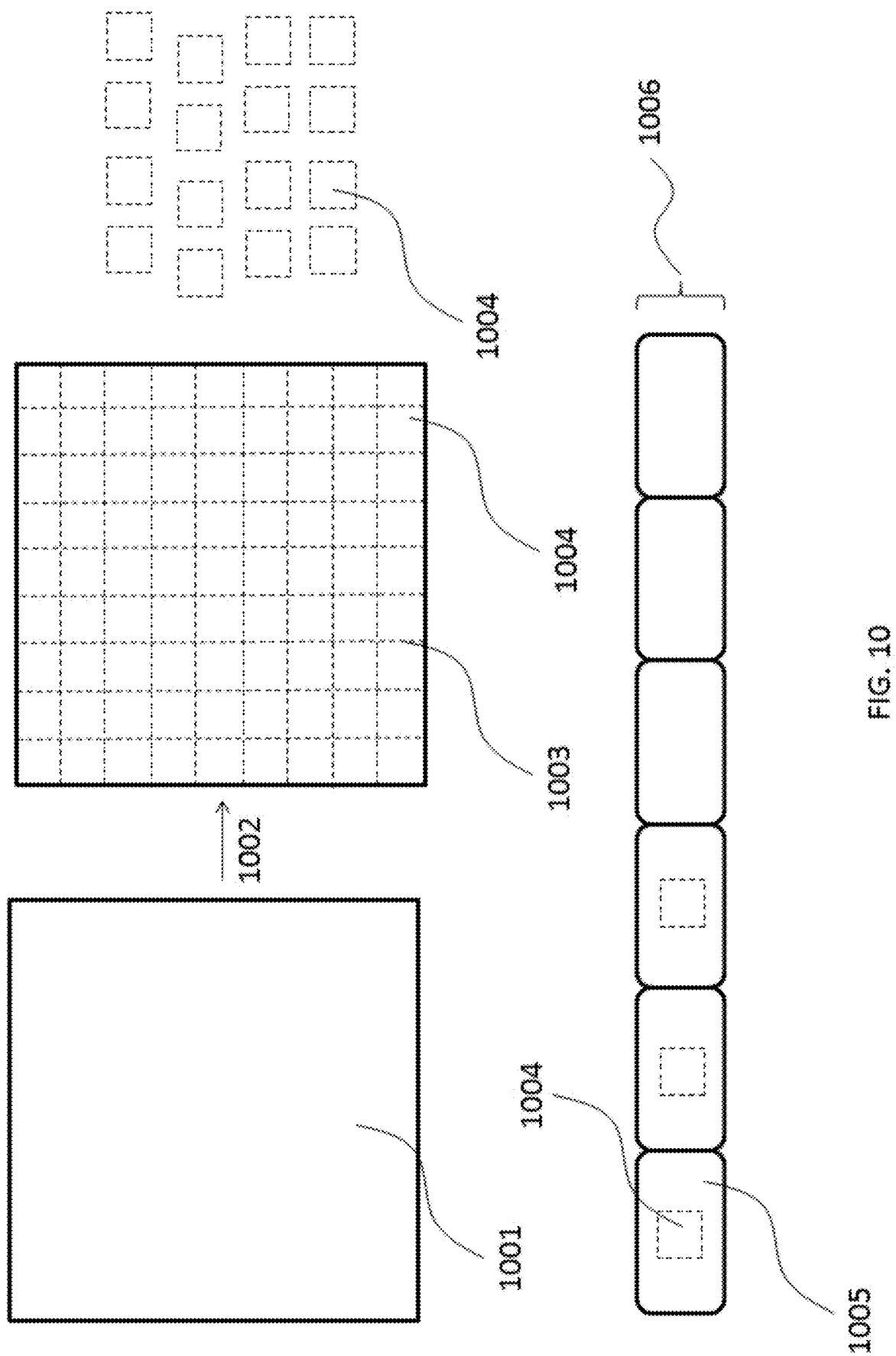
FIG. 10 is a schematic illustration of an example method according to the present invention.

FIG. 10 is a schematic illustration of an example method according to the present invention. Active detecting material (ADM) can be coated on a clear or translucent adhesive material, but another medium can be used in the manufacturing of the sensor such as an absorbent material such as white filter paper. White filter paper or any white absorbent material can reduce the likelihood of confusion or lack of ability to distinguish an activated sensor from a dark-skinned individual. In the figure, a starting medium 1001 comprises white filter paper. This material can be suitable for the creation of colorimetric sensors due to its ability to absorb and immobilize the ADM in one place. The starting medium can be separated into a plurality of sensing pieces 1002, e.g., a laser cutter can be used to cut the sheet 1001 into smaller sensing pieces, shown separated in 1004. The pieces 1004 are illustrated as square or rectangular shapes as shown by 1003 lines, but can also be cut in hexagonal or rhombic shapes. It can be desirable to use shapes that comprise adjacent or touching sides to minimize unnecessary waste when cutting is complete. The adhesive patch shown in 1005 can be manufactured in-house or obtained through a third party manufacturer. The adhesive sheets can be arranged in rolls of single-filed or multi-filed units of individual adhesive patches as shown in 1006. Once the non-adhesive backings (not shown in FIG. 10) of the adhesive sheets are peeled off, individual sensing pieces of 1004 can be placed in the center of regions of the adhesive material 1005. Then, the non-adhesive backing is re-adhered onto 1006. The finalized individual sensors 1004 are now embedded onto individual "bandage-like" patches.

Example Embodiments. Example embodiments were produced as described below. The reagents used included the following:

Assay Buffer pH 7.2, lot 161109, composition 100 mM KPi buffer pH 7.2, 40% sucrose, 0.1% BSA in dH20;

TMB dye, lot 170105, composition 0.5 M 3,3',5,5'-Tetramethylbenzidine in acetone; Sigma Aldrich Cat #860336 Lot: BCBR1884V;

Alcohol Oxidase (ALOX), lot 170105, 1.04 U/µL Alcohol Oxidase *Pichia pastoris*, Sigma Cat No: 860336;

Peroxidase, lot 170104, 20 U/µL HR Peroxidase, 100 mM Kpi pH 7.2, 40% sucrose, 0.1% BSA in dH2O;

1% ethanol, lot BF02I19, 1 v % ethanol in dH2O.

Strips were prepared as described generally above, with each strip being 5 mm×6 mm (30 mm squared area). A first group of strips were prepared with ALOX and 1× TMB, according to the following:

$1^{st}$ dry: 0.175 U/strip Sigma ALOX, 10 U/strip HRP, assay buffer pH 7.2;

$2^{nd}$ dry: 50 mM TMB in acetone.

A second group of strips were prepared with ALOX and 5× TMB, according to the following:

$1^{st}$ dry: 0.175 U/strip Sigma ALOX, 10 U/strip HRP, assay buffer pH 7.2;

$2^{nd}$ dry: 250 mM TMB in acetone.

The procedure for preparing the strips was as follows:
(1) Prepare the dipping solution, comprising 0.175 U/strip Sigma ALOX, 10 U/strip HRP, assay buffer pH 7.2.
(2) Add the dipping solution to filter paper and dry in a dessicator for at least 1 hour.
(3) Prepare 50 mM TMB and 250 mM TMB in acetone.
(4) Add 50 nM TMB to half the filter paper from step 2. Add 250 mM TMB to the other half of filter paper.
(5) Dry filter paper in dessicator for at least 1 hour.

In the description herein, TMB refers to a dye used in the formulation of colorimetric sensors; ALOX refers to alcohol oxidase; U refers to an enzyme unit; strip refers to a total area of about 30 millimeters squared; HRP refers to horseradish peroxidase.

The preceding examples provide recipes that can be used to make alcohol detection paper sensors. The specific amounts of chemicals listed can be examples of minimum amounts needed if the formulation of individual sensors. The order of the steps can be important to achieving the desired sensor characteristics. It can be important to apply and dry the TMB in acetone after the enzymes are already dried on the paper. If the TMB is dried on the strips before the enzymes (instead of after), then the unreacted sensing strips will react. Also, it can be important to prepare the TMB in acetone because of its low solubility in water, and because of acetone's low toxicity relative to other organic solvents. Preparing TMB in acetone also allows for greater concentrations of TMB than those in the examples above, if desired.

While the present invention has been described in terms of particular embodiments and applications, in both summarized and detailed forms, it is not intended that these descriptions in any way limit its scope to any such embodiments and applications, and it will be understood that many substitutions, changes and variations in the described embodiments, applications and details of the method and system illustrated herein and of their operation can be made by those skilled in the art without departing from the spirit of this invention.

What is claimed is:

1. An analyte sensing patch, comprising
(a) a substrate that is impermeable to an analyte; and
(b) a sensing agent disposed on a first side of the substrate, in a first region of the first side of the substrate, wherein the sensing agent undergoes a change in a discernible characteristic responsive to encounter with the analyte;
(c) an adhesive disposed on the first side of the substrate in a second region of the first side of the substrate, wherein the second region surrounds the first region; and (d) one or more control regions of the patch, wherein a control region exhibits a characteristic that corresponds to the characteristic of the sensing agent upon exposure to a predetermined amount of the analyte; wherein the sensing agent comprises a polyaniline film with an embedded enzyme.

2. The analyte sensing patch of claim 1, wherein the substrate comprises a polymer suitable for transdermal patches.

3. The analyte sensing patch of claim 1, wherein the substrate comprises polyurethane.

4. The analyte sensing patch of claim 1, further comprising a reader external to the patch that detects the change in the discernible characteristic.

5. The analyte sensing patch of claim 4, wherein the discernible characteristic comprises color, and wherein the reader comprises a color meter.

6. The analyte sensing patch of claim 1, wherein the sensing agent is adhesive to tissue.

7. The analyte sensing patch of claim 1, further comprising an identifier mounted with the patch such that the identifier is discernible by a reader of the patch.

8. The analyte sensing patch of claim 7, wherein the identifier is associated with a calibration corresponding to the patch.

9. The analyte sensing patch of claim 1, wherein the predetermined amount is greater than zero.

10. The analyte sensing patch of claim 1, comprising first and second control regions, where the first control region exhibits a characteristic that corresponds to the characteristic of the sensing agent upon exposure to a first predetermined amount of the analyte, and where the second control region exhibits a characteristic that corresponds to the characteristic of the sensing agent upon exposure to a second predetermined amount of the analyte, where the first predetermined amount is different from the second predetermined amount.

* * * * *